US010629298B2

(12) United States Patent
Seufert (10) Patent No.: US 10,629,298 B2
(45) Date of Patent: Apr. 21, 2020

(54) MEDICATION SCAN ACQUISITION DEVICE AND METHOD THEREOF (71) Applicant: Utopia Health Design LLC, Philadelphia, PA (US)

(72) Inventor: Regina Seufert, Philadelphia, PA (US)

(73) Assignee: Utopia Health Design LLC, Philadelphia, PA (US)

( * ) Notice: Subject to any disclaimer, the term of this patent is extended or adjusted under 35 U.S.C. 154(b) by 0 days.

(21) Appl. No.: 15/949,515

(22) Filed: Apr. 10, 2018

(65) Prior Publication Data

US 2018/0294050 A1 Oct. 11, 2018

Related U.S. Application Data (60) Provisional application No. 62/483,983, filed on Apr. 11, 2017.

(51) Int. Cl.
*G06F 7/00* (2006.01)
*G16H 20/13* (2018.01)
*G06K 7/14* (2006.01)
*G16H 20/10* (2018.01)
*G16H 40/63* (2018.01)
*G16H 20/17* (2018.01)
*G06K 19/06* (2006.01)

(52) U.S. Cl.
CPC .......... *G16H 20/13* (2018.01); *G06K 7/1417* (2013.01); *G16H 20/10* (2018.01); *G16H 20/17* (2018.01); *G16H 40/63* (2018.01); *G06K 19/06037* (2013.01)

(58) Field of Classification Search
CPC ..... G06K 7/016; G06K 7/0166; G06Q 10/087
USPC ........................ 235/376, 385, 462.01, 472.02
See application file for complete search history.

(56) References Cited

U.S. PATENT DOCUMENTS

| 5,032,112 A | 7/1991 | Fairchild et al. |
| 5,492,247 A | 2/1996 | Shu et al. |
| 5,845,264 A | 12/1998 | Nellhaus |
| 8,297,473 B2 | 10/2012 | Smith |
| 8,560,345 B2 * | 10/2013 | Wehba .................. A61M 5/142 705/3 |

(Continued)

OTHER PUBLICATIONS

Pilkington et al., U.S. Appl. No. 15/216,385, filed Jul. 21, 2016.

(Continued)

*Primary Examiner* — Daniel St Cyr
(74) *Attorney, Agent, or Firm* — Caesar Rivise, PC (57) ABSTRACT A medication scan acquisition apparatus comprises a scan initiator for permitting acquisition of scanning identification information obtained from a medication storage container, the identification information associated with respective medication selectively included with the medication storage container; an attachment member to which the one of the plurality of medication storage containers is attached; and a medication storage container detector for detecting presence of said medication storage container when the medication storage container is attached to the attachment member, wherein the scan initiator permits acquisition of the scanning identification information responsive to the medication storage container detector detecting the presence of the medication storage container.

20 Claims, 7 Drawing Sheets

(56) References Cited

U.S. PATENT DOCUMENTS

| | | | | |
|---|---|---|---|---|
| 2004/0193453 A1* | 9/2004 | Butterfield | ............ | A61M 5/172 |
| | | | | 705/2 |
| 2005/0277890 A1* | 12/2005 | Stewart | ................ | A61M 5/172 |
| | | | | 604/189 |
| 2006/0229551 A1* | 10/2006 | Martinez | ............... | A61M 5/172 |
| | | | | 604/67 |
| 2007/0214003 A1* | 9/2007 | Holland | ................ | G06F 19/326 |
| | | | | 705/2 |
| 2007/0233049 A1 | 10/2007 | Wehba et al. | | |
| 2014/0262918 A1 | 9/2014 | Chu | | |
| 2017/0074717 A1 | 3/2017 | Pilkington et al. | | |
| 2017/0076060 A1 | 3/2017 | Pilkington et al. | | |

OTHER PUBLICATIONS

Pilkington et al., U.S. Appl. No. 15/216,488, filed Jul. 21, 2016.
Alaris Model 8015 Operations Manual, pacificmedicalsupply.com/alaris-8015-pc-unit-infusion-pump/, Pacific Medical 2017.

* cited by examiner

(PRIOR ART)

MEDICATION SCAN ACQUISITION DEVICE AND METHOD THEREOF

This application claims priority to U.S. provisional application No. 62/483,983 filed on Apr. 11, 2017 which is hereby incorporated by reference in its entirety.

FIELD OF THE INVENTION

The present invention relates to intravenous pumps and more specifically to safety features for use with intravenous pumps. In particular, an intravenous pump and method thereof include scanning and intravenous bag sensing in order to improve patient safety.

BACKGROUND OF THE INVENTION

A conventional IV pump is programmed to deliver liquid medication. Such medication is hanging in containers (such as bags) from separate IV poles above the pump. The liquid medication leaves such containers at a controlled rate and is connected to an IV pump channel via IV tubing. As the medication leaves the IV pump channel, the medication is infused into the patient via intravenous access.

An example of a conventional IV pump is the Alaris PC Unit, Model 8015, Software Version 9.19, which is known to one of ordinary skill in the art. Such an IV pump may be used in combination with a pump module, such as the Alaris Pump Module 2426-0007, which is known to one of ordinary skill in the art. The PC unit may be used in combination with IV tubing, which is well known. An IV pump may be connected to an IV pole via a clamp—an exemplary method of connection is documented with reference to the documentation (available at www.bd.com) associated with the Alaris PC Unit, model 8015, which is hereby incorporated by reference in its entirety. IV channels may be connected to IV pump electronics via IUI connector which is known to one of ordinary skill in the art.

In most hospitals, a system is in place so that medication is scanned at a computer that is in a location different from, and separate to, the pump. Once the medication has been scanned, an IV pump user then programs the pump.

While some medication scanning systems are known in the prior art, several hospital systems report a lack of compliance with medication scanning, especially during emergency situations or in departments such as the emergency room.

Handheld scanners are also known, for scanning medications in a hospital setting, but those scanners may increase the risk of bacterial contaminations, since health care professionals touch such scanners several times throughout the day. Unwashed hands quickly create problems create and/or come in contact with multiple contaminated surfaces. Handheld scanners can thus contribute to increased contamination and infection risks.

Prior art IV poles allow medication to be hung in a manner that may contribute to medication dispensing errors. Thus, a possibility exists that medications will be confused, and wrong medications will be dispensed to a patient. Furthermore, current designs place patients at risk as a result of errors caused by for improperly diluted infusion. For example, IV potassium non-diluted may be connected to IV Normal Saline 0.9% in a piggyback fashion. Improper placement of medication, confusing placement of medication, and improper clamping of IV tubing (above the IV pump, for example) can result in medication error and undiluted medication infusion. Such an error may result in the infusion of non-diluted medication, with a result of a fatal heart dysrhythmia, and subsequent death.

In prior art, the pump may have scanner scan pump channel bar code technology to recognize if correct medication is connected to pump channel being programmed. Technology exists to scan the channel in which the medication is being connected to ensure proper medication is infusing in proper channel programmed below.

In one prior art configuration, the IV pumps are separate from the IV pole. The IV pole is designed to hang IV fluids that are to be infused into a patient's vein, or fluids may also be used for administration via other routes, such as intra-arterial, epidural, etc. The rate at which the infusion occurs is controlled by an IV pump based on the operation of hardware and software within the pump. The medicine being infused is desirably hung from a location that is higher than the pump so as to use gravity to push the fluids from the IV bag into IV tubing. In some emergent situations, bags of IV fluids are hung and the medication therein flows by gravity without a pump. In such situations, the drip rate may be manually set my hand, and the drip rate may be set based on skill. Administering medication by gravity in such a manner, and without a pump, poses many safety risks.

In the prior art, one known method is for software to prompt a user to scan a medical provider's ID badge and to then scan identification information (i.e. a bar code) attached to a patient. This may be done with a hand held scanner. This technique is intended to ensure that the correct medication is being delivered to each patient. In such a prior art system, audible and visual alerts with alarms, reminders, and other forms of user interface may be used to improve quality of care.

Software upgrades of prior art may include safety reminders on interfaces to remind IV pump users of evidenced based practice, and integration of pharmacy specific infusion instructions.

Software upgrades may include improved safety guardrails for medication infusion information. The safety mechanisms, as well, can assist to try to prevent incorrect medication rates, as incorrect rates can be fatal.

Electronic medical record (EMR) software can display error messages when scanning indicates that an error is about to occur (such as wrong medication scanned, wrong patient, wrong time, etc.).

An LCD screen of channel displays may indicate the letter of the channel that the PC communicates with (e.g. A, B, C, D, as described by Alaris).

An IV pump main computer PC may be connected to an IV channel. Data from a scanner and bar code may connect wirelessly or via wired connection or cord to hospital EMR in order to enhance safety procedures. Data from scanner on channel in Alaris model may connect via IUI connection as seen in prior art.

SUMMARY OF THE INVENTION

A medication scan acquisition apparatus comprises a scan initiator for permitting acquisition of scanning identification information obtained from a medication storage container, the identification information associated with respective medication selectively included with the medication storage container; an attachment member to which the one of the plurality of medication storage containers is attached; and a medication storage container detector for detecting presence of said medication storage container when the medication storage container is attached to the attachment member, wherein the scan initiator permits acquisition of the scanning identification information responsive to the medication storage container detector detecting the presence of the medication storage container.

DETAILED DESCRIPTION

A medication scanning device may connect with a horizontal IV pole with a plurality of hooks (or other attachment members), hung above an IV pump, and connected with a vertical IV pole. Each IV pole hook on horizontal pole optionally including a connection to an internal switch inside medication scanner configured to activate the 2D bar code scanner when internal switch(es) detects presence of a new IV medication bag or IV medication fluid bag. In one exemplary embodiment, presence of an IV bag is detected as a result of a measurement switch being activated, wherein the switch is activated by the weight of the IV fluid and container/bag. In one exemplary embodiment, a horizontal IV pole housing, which is connected to a hook, moves which presses on a spring. This action in turn activates a button or switch. As a result of the activation, input from scanner is accepted. Horizontal IV pole may move along a track internally inside a larger vertically IV pole which connects in a perpendicular fashion. Each IV pole hook and horizontal pole connects with the internal switch for acceptance of data by the scanner. The scanner may be placed above IV pump and in a position to scan.

The medication IV pump scanner increases safety measures with regard to IV administration of medication. For example, by an IV pump user such as a medical professional scanning as explained above, IV pump rate may be programmed based on a scanned bar code/2D bar code. Medication presence (i.e. weight) causes activation of an internal switch. Subsequently, 2D camera scanner may be used (or may be activated) to measure bar code and/or 2D bar code. The combination of the medication presence detection and the scanning enables a medical professional to program the IV pump channel (also known as administration sets) as further explained below. The change in the amount of fluid medication in the medication bag/container changes the tension on the internal spring pressing on the internal switch, proximity or pressure sensors connected to spring. This notifies the IV pump software that the medication is infusing based on tension of the spring decreasing (and proximity changing). Failure of the spring tension to change would notify a user that the user IV tubing may be clamped above IV pump, or below IV pump, or it may indicate that there is some other obstruction to flow. Scanning device may also be used to configure the pump for intravenous (IV), intra-arterial (IA), subcutaneous, epidural delivery.

In an exemplary embodiment of the present invention, an internal switch inside IV medication scanner housing is activated. Such activation, when combined with scanning from, for example, a 2D medication scanner, may also be accompanied by programing an IV pump in order to administer a dose of liquid intravenous medication and/or IV fluid. Such programming may be by bar code or 2D bar code. In an exemplary embodiment of the present invention a housing is arranged with a 2D camera therein. The housing may be connected to a hollow IV pole, from which medication is hung (on a hook for example) which is connected to the hollow pole. In this manner, activation of an internal switch by the force of gravity (by placing medication or fluid on IV pole hook), moving the horizontal pole pressing on an internal spring activating the switch, may signal a 2D camera to take a picture of a medication bar code or 2D bar code. This may result in programming the IV pump as explained below. Thus, software is programmed to recognize bar code or 2D bar code. Such recognition may be based on information from a manufacturer/internal pharmacist or other source, or from another method of labeling. The mechanism of the internal switch that is connected to a pole from which medication is hung, saves time, and allows for compliance to IV fluid safety protocols. Medication scanners, in pair of two (for example), in a vertical column (for example), are connected via data transfer cables, inside hollow IV pole to each scanner in the column and to the IV pump computer PC. Alternatively, scanners may communicate wirelessly with a wireless network connection. Two scanners in a vertical column, for example, allows for medication scanning compliance with piggyback medication infusions, when two fluids or medications connect via IV tubing above channel/IV pump. A switch is contained in medication scanner housing which is activated by the gravity/force/pressure/weight of the medication on the metal hook portion of IV pole for generating user interface information on the display areas of IV pump scanner and programming pump infusion rate. Information regarding the programming may be displayed on the IV pump channel interface screen as well. The power from the device is from an electrical circuit such as from a wall outlet, or from connection via cables to a battery in IV Pump PC. All components including 2D camera, IV pump channel, internal switch, proximity sensor, hollow IV pole and hook, connect via electrical wires, data transfer cables and inter-unit interface (IUI) connectors. The switch activated by the pressure/gravity from the weight/mass of medication or fluid, and the use of a scanner enables detection of the right medication, right concentration, and right dose as well as rate via information on bar code and integration as described in prior art. Failure to use the medication scanner, bypasses safety features which can result in harm and fatalities based on human error.

Alternatively, an exemplary embodiment of the present invention relates to an internal magnetic switch inside an IV medication scanner housing. The switch is for activating a 2D medication scanner for programing an IV pump to administer a dose of liquid intravenous medication and/or IV fluid communicating with an IV pump. In this manner programming is achieved by bar code or 2D bar code from manufacturer medication packaging. The exemplary embodiment comprises: a (square) housing arranged with a 2D camera therein, to connect to a modified hollow IV pole, in which medication is hung on a hook connected to a hollow pole, for activation of internal magnetic switch activated by force of gravity. This is achieved by placing medication or fluid on the IV pole hook, moving the horizontal pole, and thus moving the magnet on the pole closer to activating a magnetic hall effect sensor activating switch to an "on" position when the magnet moves at perpendicular angle, so that a 2D camera takes a scan/picture of medication bar code or 2D bar code.

Proximity sensors located at ends of spring inside medication housing and are able to detect whether medication IV tubing is mistakenly clamped above the IV pump channel. When the proximity sensor moves farther apart while active infusion is programmed, software will be notified that IV fluid or medication is infusing. If proximity sensors do not change in location after pressing infuse or start button as described, IV pump interface notifies IV pump user that the medication is not infusing, and to check tubing clamps or other causes of flow obstruction based on communication and integration with proximity sensors inside the medication scanner.

Ease of use for IV pump users is improved, as well as improving patient safety and decreasing patient harm. Thus, compliance to safety features of an IV pump are improved, and safety concerns are addressed. This is because errors as a result of human error and/or lack of compliance are inevitable. Compliance with safety features is improved, since bypassing safety features in prior art is easily performed, due to lack of time or by choice as well as other contributing factors.

An exemplary embodiment of the present invention relates to a medical device such as a manually programmable IV pump by the IV pump user. In a further exemplary embodiment, an IV pump includes features in order to decrease medication errors via intra venous route (medication in liquid form administered sterile into the vein at controlled rate by pump) by enhancing quality of care by IV pump user. In one exemplary embodiment, an IV pump is includes exemplary software and hardware in order to decrease medication errors. An exemplary embodiment of the present invention relates generally to medication error prevention designed to improve compliance with hospital protocol and evidence based practice related to proper handling of IV pump, Intravenous medication, fluids, and supplies. An exemplary embodiment of the present invention relates to prevention of medication error by enhancing IV pump user compliance with design using features including one or more of the following exemplary features: sensors, IV pump, software and hardware upgrades, medication scanner, 2D bar code, bar code, 2D camera, IV pole, lcd screen and user interface, data connection cables, bar coding medications. In one exemplary embodiment, standardization of IV medication scanning is obtained in order to increase compliance to scanning and safety feature to determine clamping of IV tubing to ensure patient safety and proper infusion of IV medication.

Design improvements are made to increase compliance to safely administer medication. Medication 2D camera communicates with IV pump to program the pump via data communication cables as an example, and is connected to internal switch. Scanning cannot be bypassed based on location on the scanner and the switch activation by the organic placement of the IV fluid or medication.

All IV medications have the potential to be high risk when administered at wrong rate, concentration, route, time and to the wrong patient. Special attention must be paid to all IV infusions.

In rushed hospital and acute care work environments, there are several factors that can decrease the likelihood of medication scanning and attention paid to IV medication infusions proper handling.

The disclosure provides for a medication scan acquisition device. The medication scan acquisition device may include a plurality of hooks or other attachment members, each hook including connecting to a pole which activates an internal switch configured to turn on 2D camera/scanner detected by pole movement, based on weight placed by medication or fluid. By "turn on" what is meant is that the process of scanning the outside of an IV bag to obtain therefrom is initiated. More particularly, what is being started is the acquisition of information. When acquisition is started, data this is obtained from scanning an IV bag may be used to program an IV pump, and/or to determine whether correct medication in the IV bag is being dispensed. Alternatively, the information may be used to set flow rates, timers, etc. Internal switch intended to activate camera to notify IV pump new medication hung. Weight sensing switch can detect when medication hung and removed from IV pole hook Internal switch, by force placed on switch or removed from switch. The switch itself is not necessarily measuring weight (although weight measurement may optionally occur). The switch may be a simple on/off toggle switch that is switched to "on" when an IV bag is hung on the hook. Such a switch may be spring loaded, for example, so that it is urged into an open position when no bag is hung on the hook, and subsequently the weight of the bag on the hook compresses the spring and closes the switch. Alternatively, the "switch" may have another form, such as a proximity switch (explained below, or in addition to the proximity switch explained below), an angular measurement switch, piezoelectrics, etc. Each hook is placeable on an IV pole above IV pump and IV pump channels. The medication scanner may include a user interface configured to provide medication name and rate of each medication. User interface screen faces IV pump user, placed above IV pump interface of IV pump channel interface. The disclosure also provides methods for scanning medication and detecting error of IV tubing clamped above pump in piggyback infusion.

The medication scanner connected to the weight sensing switch with software upgrades and proximity sensors is intended to make infusions of IV medications safer for the patient and easier for the healthcare professional.

Current therapies for Intravenous infusions include medications for a large array of illness and would affect a majority of hospitalized patient requiring IV hydration and infusions. The medication scanner with weight sensing switch replaces the need for the IV pump user to manually program the pump, and also replaces the need for the healthcare provider to take an additional step to pick up a scanner or to scan in another location of the pump, or connection to IV PUMP via scanner on channel in prior art. The current scanning methods are often time consuming because it is an additional step to be taken, and can be bypassed. An IV medication is placed on an IV pole hoke for an infusion, naturally.

The IV medication or fluid is desirably higher than the IV pump. Placing the scanner in a place to communicate with the medication on the hook, saves time and prevents non-compliance with medication scanning which often results in medication infusion error often caused by human error. The placement of the scanner as well as the internal mechanism with switch, removes the step of placing the medication in another location to perform the scanning before the final destination of the IV pole hook placement. This overcomes many disadvantages of previous devices.

The "weight" sensing switch is able to detect when a new bag of IV fluid is hung, therefore ensuring increased compliance with scanning IV medication or IV fluid bar code with new medications and fluids as well as when replacing continuous infusions. It is common to skip medication scanning during continuous infusions. Software and statistics often miss this issue with noncompliance because it is not easily detected with current software and design as seen in prior art.

In place of a weight sensing switch, a contact switch may be sufficient in some exemplary embodiments. Thus, if the weight of the bag is sufficient to activate the switch, this may indicate that the IV bag is present. A lack of sufficient weight may prevent activation of the switch, indicating that no bag is present. A transition from activated to non-activated may indicate that the medication is leaving the bag. Lack of a transition from switch activation to switch non-activation may indicate the medication is not flowing out of the bag.

The proximity sensor inside medication infusion housing is able to detect if medication is not infusing with piggyback medication, for example, via lack of tension change on spring where proximity sensor is located. Proximity sensors document error, with notification or error on IV pump main interface. Error does not allow medication or fluid to flow through channel until error is fixed. This prevents a non-diluted medication from infusing into patient or from a missed medication dose from clamping the medication.

Figure 3A:
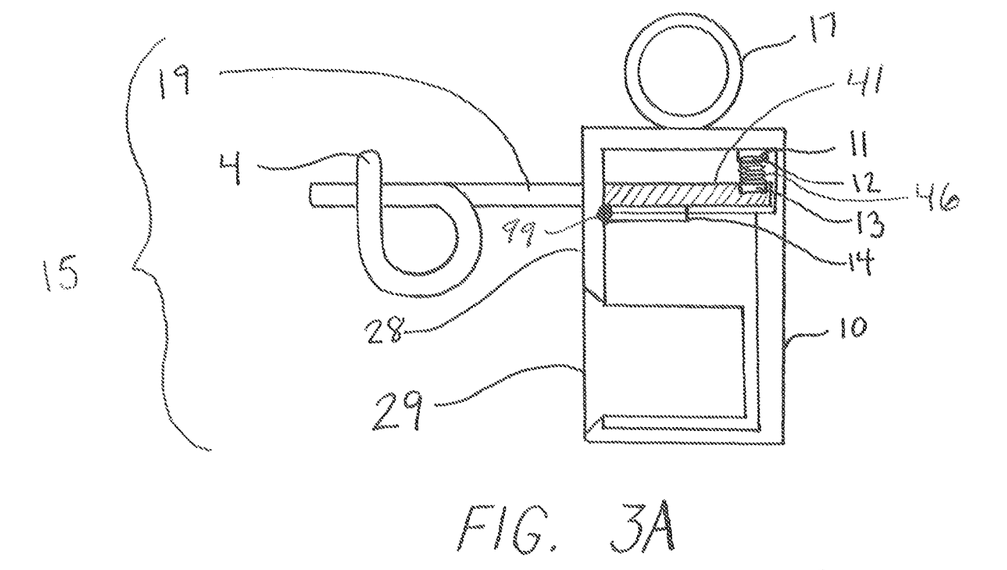
FIG. 3A and FIG. 3B are side views of portions of the IV scanner illustrated in FIG. 1.
Figure 3B:
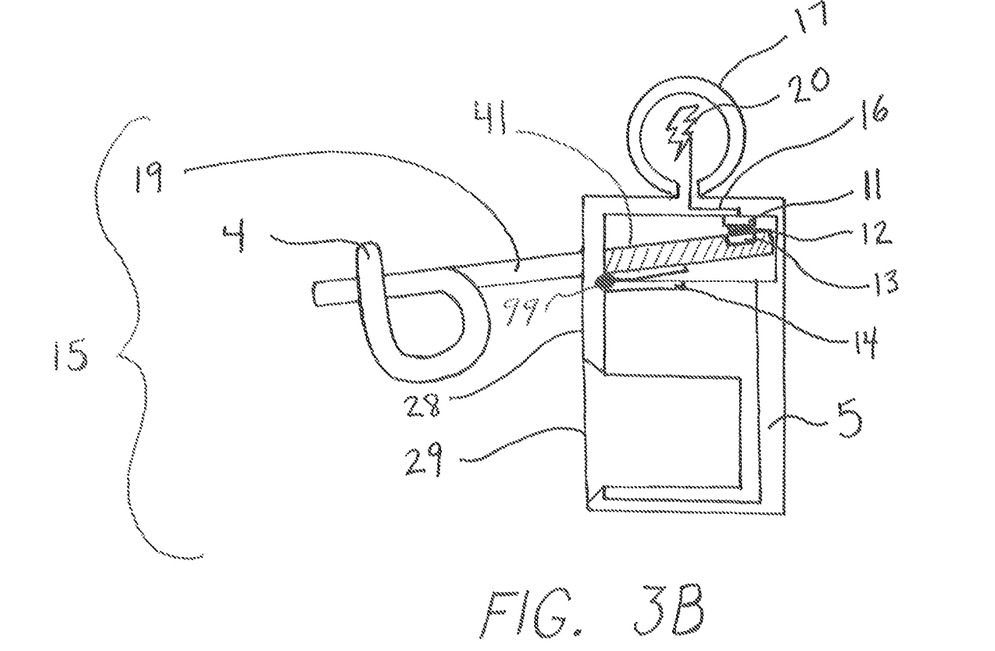

The proximity sensor in relation to a magnet, will emit an electromagnetic field or a beam of electromagnetic radiation, and the hall effect sensor will look for changes in the field or return signal. In the case of the medication scanner, the object is sensed (or target) as a result of upwards and downwards motion (changes) of the position of pole or apparatus, which also causes change in voltage between sensor and magnet shown in FIG. 3B. A Hall Effect proximity sensor has three pins, which is a is microvolt supply pin, a ground pin, and is sensor output pin. Hall effect sensor and 3 pins is embedded inside a stationary plastic housing that acts as a switch, connected to the scanner to collect data via wires (for example), to transmit data from the camera via data transfer cables to IV pump PC. The scanner connects to the IV pump PC via data transfer cables inside the IV pole as an example of connection. Hall effect sensor pins connect via thin wires to relay system or solid state technology such as an Arduino or programmable logic controller inside the IV medication scanner housing, which connects to the scanner camera via wires. Scanning collects data with each scan which connects to IV pump scanner pump channel via data transfer cables to main PC (for example USB, CAT6, CAT7, custom cable, proprietary cable) which connect to IV channels via IUI connection. Horizontal IV pole 19 moves with magnet closer to hall effect sensor when medication is hung on pole hook, when the Hall Effect sensor is on, so that hook movement within range is detected by hall effect sensor. The magnet sensor communicates with the hall effect sensor. The Hall Effect sensor connects to 3 thin wires that are insulated. The sensor detects magnetic field and turns the switch on. A Hall effect sensor is a transducer that varies its output voltage in response to a magnetic field. There is a voltage supply pin of hall sensor, ground pin of hall sensor, sensory output pin of hall effect sensor. The magnetic field shown in FIGS. 3A and 3B is created by magnet on IV pole 19 away from most distal to hook, in relationship to the Hall Effect sensor embedded in the IV scanner housing, which is connected to the power source via data transfer cables integrated in the IV pole which connect to 3 pins of hall effect sensor. The magnetic sensor meets the Hall Effect sensor at the south end of the magnet, wherein the north end of the magnet is on top (in one exemplary embodiment).

Two medication scanning devices may be placed (for example) in a vertical column communicating with IV pump below to account for noncompliance with piggyback infusions, and misplacement of piggyback infusions. Software understands that the infusion is infusing properly when both medication scanner internal proximity sensors move further apart simultaneously. When fluid medication flows properly, tension on spring decreases and proximity sensors move further apart, notifying infusion software of proper infusion, and lack of clamping above pump. In the event of a proper infusion, screen interfaces on IV pump channel would display proper infusion as shown in prior art. The likelihood of delivering an incorrect medication or an incorrect rate or dilution are reduced by this design. The medication scanner connected to weight detecting switch automatically programs the IV pump rate by the integration of the IV pump technology upgraded to connect the hospital electronic medical record, with the 2D bar code or bar code from the medication manufacturer or other bar coding source.

Prior to the medication administration, the medication is labeled either from manufacturer with a standard placement of the bar code or 2D bar code on the IV fluid or medication, or placement of bar code from pharmacist. The position of the label aligns with the scanner inside medication scanner housing. Shape and dimensions and proportions of the accompanying drawings may not be to scale, but are intended to display the concept of the principle of the scanning method, and safety features. Thus the drawings do not represent definitive design for proportion, or placement of labels based on hospital pharmacy protocol. Relationship and distance from medication scanner to hook can vary. The interface may remind the IV pump user to reposition bar code if the 2D camera/bar code reader is unable to detect bar code, based on positioning or other factors affecting clear imaging of bar code.

The medication scan acquisition device has two functions. Once the weight (or presence detecting) sensing switch detects that a IV fluid of medication has been hung, upon activation by the weight sensing switch, the 2D camera is turned on (meaning, at a minimum the acquisition of data associated with the bag is initiated—the acquisition can occur at the camera, or at other locations such as at the pump a point is programed, or even programing of the pump is executable) and takes a picture of the 2D bar code of medication or bar code of fluid. Thus, the switch is an example of a portion of a medication storage container detector for detecting presence of the medication storage container when the medication storage container is attached to an attachment member such as a hook. When the scan initiator (that permits acquisition of scanning identification information obtained from the medication storage container, the identification information associated with the respective medication selectively included with the medication storage container), permits acquisition of the scanning identification information responsive to the medication storage container detector detecting presence of the medication storage container. The second function, is monitoring the tension on the spring which has connection to proximity sensors on edges of spring. A sensor associated with a spring, for example, monitors spring tension by proximity or proximity sensors. As medication or fluid is infusing, the tension on the spring changes and decreases, notifying the IV pump that the medication is infusing properly. If there is tension on a spring, and distance between proximity sensors does not change after IV pump user has pressed the infuse or start button, in one exemplary embodiment the software stops that channels infusion and prompts IV pump user to check the clamp above the IV pump. In other embodiment, a warning is given.

The IV tubing of medication and/or fluid is placed in the pump channel below 2D camera linearly in the same column, for example.

In an aspect, an exemplary embodiment provides a medication scan acquisition device and devices. The medication scan acquisition device includes a plurality of hooks, each hook connects to a mass/weight detection feature, such as an internal switch configured to detect a medication contained on the respective hook, each hook being placeable above IV pump to dispense and automatically program pump rate, infusing IV pump medication, intra-arterial medication or epidural medication. Medication scanning device connected to IV pump in this model by data transfer cable connections inside IV pole as an example to connect to pump PC and IV pump channel hardware and software. Data transfer from IV medication scanner to channel and IV pump PC may connect with data transfer wires outside of IV pole as well. Medication scanner placed above IV pole on hook may attach wirelessly, and have charging station, or connect via data transfer cable and charge via internal battery of IV pump PC as described in prior art. The medication scanning device further may prompt the IV pump to display a user interface configured to provide instructions with regard to scanning medication and scanning patient wrist band as described in prior art. Based on removing medication mass/weight of the medication placed on the internal switch, IV pump will recognize when liquid fluid or medication has been removed. When weight detected by, scanner activates and programs pump PC and pump channel, prompting IV pump user to follow protocol of scanning to adhere to safety features as mentioned in prior art.

In another aspect, an exemplary embodiment provides a medication scanner activator by a switch. The medication activator switch may include a distal weight on horizontal pole, which pressed on a spring, activating a switch. Medication and/or IV fluid weight is greater than weight inside distal end of horizontal pole. Weight on distal end of pole places horizontal pole at an equilibrium when no medication is on the pole hook. Proximal end of pole is where medication is hung. The medication container may further include a vertical track forming a press fit with horizontal weighted IV pole, the spring and the internal switch. Horizontal pole may pivot on hinge inside medication scanner housing.

In another aspect, the disclosure provides a method and/or apparatus of detecting the dispensing and infusion of IV liquid medication. The method or apparatus may include receiving medication infusion information from proximity sensors on an internal spring. The method may further include prompting a user to unclamp IV tubing, if tension on spring does not change, and distance between proximity sensors is not detected, after IV pump user has selected infusion to start. The method may also include determining proximity of spring and tension, which will decrease tension and increase distance between proximity sensor when IV liquid or medication bag or fluid from bag or container infuses into patient, decrease fluid volume and weight, therefore moving horizontal pole, which changes position of proximity sensor on spring connected to horizontal pole and weight activated switch.

Upon learning about the practice and errors that occur in clinical practice, the novel features address these aspects and will be explained.

Thus, a weight sensing switch integrated with a 2D bar code medication scanner, connected to IV pump technology may increase compliance with scanning medication and IV fluid bar codes.

In a further exemplary embodiment of the present invention, a 2D Camera connected IV pump via data transfer cables in IV pole will make it desirable for a user to program a channel directly below a unit with a 2D camera as an example. The medication scanning device can be applied to a variety of IV poles, the linear pole poses as an example. The 2D camera for the IV medication or IV fluid is built into the medication housing and located directly above the channel in which the medication will be programmed on IV pole. Nurse or IV pump user will not program in rate or medication—setting of pump rate will be set by already existing integration with EMR, existing safety guard rails built into pump software pharmacy data, 2D bar code or bar code and scanned by 2D scanner (for example). IV pump connects via wirelessly or via cable to network connected to EMR as described in prior art. In the case of a medical emergency when a patient needs a bolus, this new design allows for the 2D bar code to be scanned by convenience of design.

The weight sensing switch in the medication scanner housing box activates 2D camera when medication is hung on IV pole. The switch is a power source for the camera to turn on and take picture or scan. This is a switch-mode power supply to the camera connected via data transfer wires inside housing. This design allows for increased medication scanning compliance. Already existing technology, scanner can detect when settings match electronic medical record order and the software will program the pump accordingly as described in prior art.

The weight sensing switch is able to detect when the volume of the bag changes and documents patient fluid is infusing properly. The software will be able to detect if the fluid bag is clamped above the IV pump, which is not an available safety feature in prior art. In current design when medication is "piggy backed" the medication can be connected to a fluid bag but the medication may be clamped, and only the fluid infuses, or vice versa. This delays patient care and results in an error. The current IV pump is not able to recognize this error in prior art. Current IV pumps cannot recognize when a fluid is clamped above the pump during piggy back infusions. Accuracy of piggyback infusions depends on properly placing primary and secondary infusions in the correct locations, at the correct distance apart. The medications may not be placed correctly, for example, and the fluid may be placed in a higher position than the medication. If the fluid is clamped above the IV pump, the medication can infused into the patient without a properly dilution which can result in patient harm or a fatality.

Software upgrades connect to medication scanners in column/vertical position communicate with each other specifically for piggyback infusions including primary and secondary infusions to notify IV pump user if medications placed on hooks are in correct place.

The design of the pump increases compliance with safety measures to prevent medication errors by increasing compliance of scanning medication, programming medication via 2D bar code, notifying IV pump user of clamped medications above IV pump (i.e. whether there is patency) and integration with EMR. The design increases integrity and accountability of healthcare professionals.

The IV Pump medication scanner with hooks that hold the fluid Bags bags/containers of medicine or fluid, may optionally be designed to have eight internal switches (for example) capable of detecting the weight of each of the IV Bags when hung from a pole hook designed to have eight hooks for example. These internal switches are components of measuring devices that, for example, monitor and gauge forces of compression, tension and shear. The switches communicate to a computer system by sending weight data by converting mechanical force in combination with magnetic field into an electrical output signal. These sensing switches are used as a type of communicator for the Pump, and may activate the 2D Camera to take a picture of 2D bar code or IV fluid bar code (or some other form of identification). The switch connects to specific IV channel. LCD display of scanner matches lcd display of channel in which medication of fluid tubing is inserted.

Medication scanning device with integrated safety features may be connected to variety of differently shaped IV poles and IV pole designs. The linear design is as example of how the medication scanner device may be placed on IV pole, connecting to already exist IV pump and channels described in prior art.

The spring inside the medication scanner housing is subject to deformation. The resulting pivoting of a portion of the IV pole apparatus that supports the IV bag may be measured. This measurement may be used to indicate if and at what rate fluid is leaving the IV bag over time. For example, a changing distance between proximity sensors as the portion of the IV pole pivots may be converted into electrical signals in order to measure the amount of pivot (if at all). For example a sensor on a spring may notify the IV pump PC that a channel (such as the channel below) should be actively infusing a medication and tension on the spring should be decreasing. Weight sensing switch can detect when new bag of fluid is hung on pole, and will reprogram pump when weight sensing switch detects bag removed and replaced. A toggle switch to indicate presence or absence of a bag with medication may also be used. Software associated with the IV pump can recognize IV fluid actively infusing to prevent error of clamping tubing above IV pump which is novel. Lack of change in proximity sensors location on the spring will notify pump software when medication is not infusing if IV tubing is clamped above pump (with a resulting lack of patency).

Error message and safety alert will appear on lcd screen on back of 2D Camera facing IV pump user when wrong medication is scanned and will not allow medication to infuse into the patient. Error message exists in EMR software with error message when wrong bar code detected, or for other errors.

Medication 2D camera scanner on pole allows for medication to be programmed on channel directly below 2D camera unit for example. Programming of IV pump based on information included in 2D bar code and bar coding. The software upgrades will allow for guardrails to be in place with pharmacy recommended guidelines into software. In case of emergency and inability to scan patient wrist band, or if band not available, infusion will infuse at correct safe pump rate based on bar code scan and other safety software upgrades mentioned in prior art.

Figure 1:
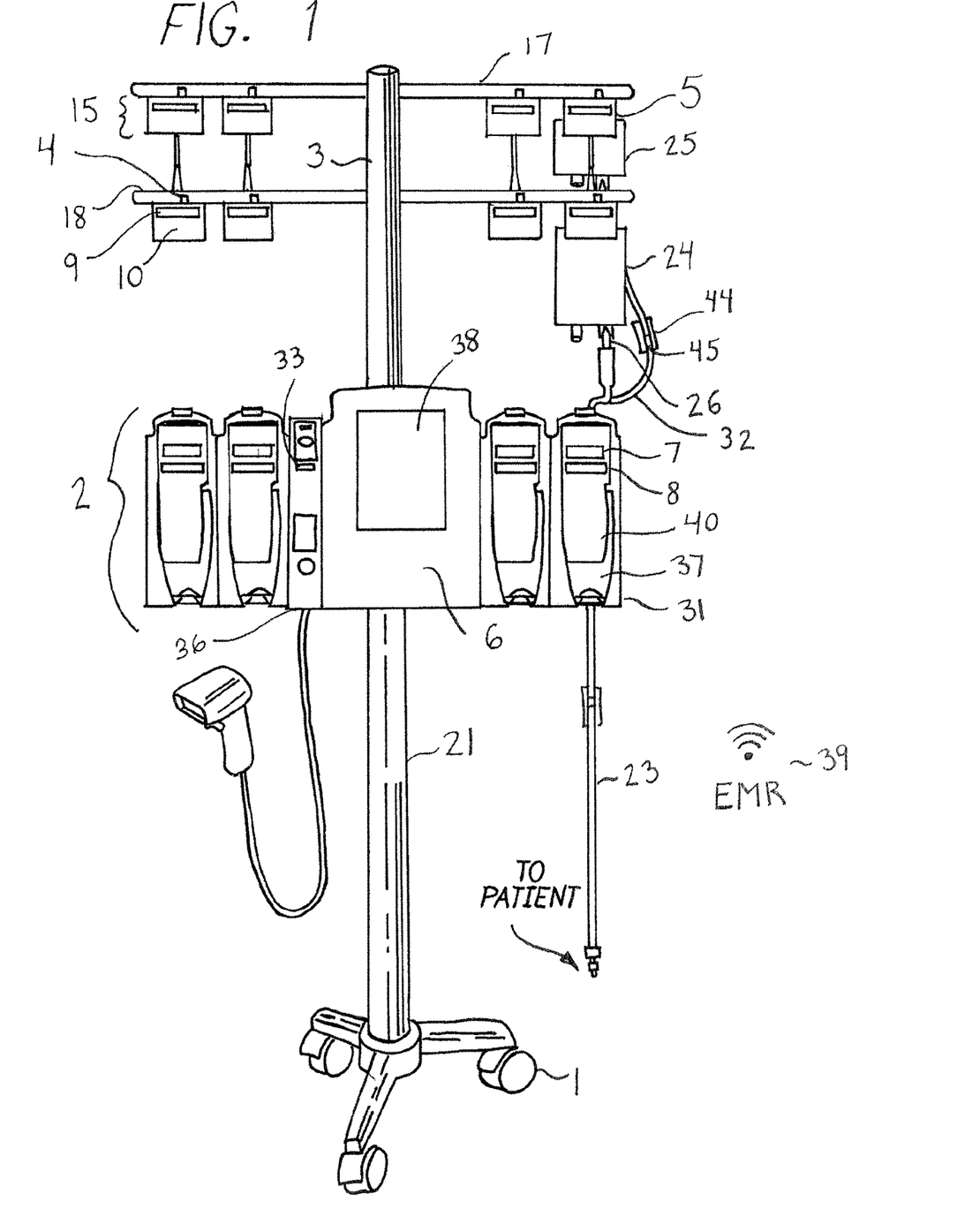
FIG. 1 is a front view of an IV pump in accordance with an exemplary embodiment with the present invention.

In at least one embodiment, the following steps are used within the system, but can occur in variety of order:
 a. Place IV bag, with primed tubing to IV pole on hook with internal switch activated by gravity from the weight of the medication triggering the switch by pressure on horizontal pole
 b. Weight from medication IV pole hook activates weight sensing switch with activates 2D Camera to scan 2D bar code or bar code
 c. Bar code connects to IV pump below to program pump or designated connected IV channel with a variety of ways to identify, channel bar coding, wired/data transfer cable(s) or wireless connection
 d. IV pump channel door opens and IV tubing is placed inside channel
 e. IV pump channel door closed by IV pump user
 f. IV pump user presses button to start infusion once all 5 rights verified by machine hardware and software, as mention in prior art, and once IV tubing connected to correct patient infusion site
 g. Pump begins infusion rate based on electronic medical record integration orders and scan of manufacturers 2D bar code or bar code
 h. IV pump notifies IV pump user if medication is not infusing based on weight change of bag detected by proximity sensor-notified IV pump user if medication clamped above IV pump An exemplary medication scanning device is pictured in FIG. 1, FIG. 2, FIG. 3A, FIG. 3B, and FIG. 4 in a variety of angles. FIG. 1 depicts how a medication scanning device communications with PUMP PC and channels. Medication scanner device can connect to a variety of different IV pole designs, and is not limited to the one displayed in FIG. 1, FIG. 2 and FIG. 3A, 3B.

Figure 2:
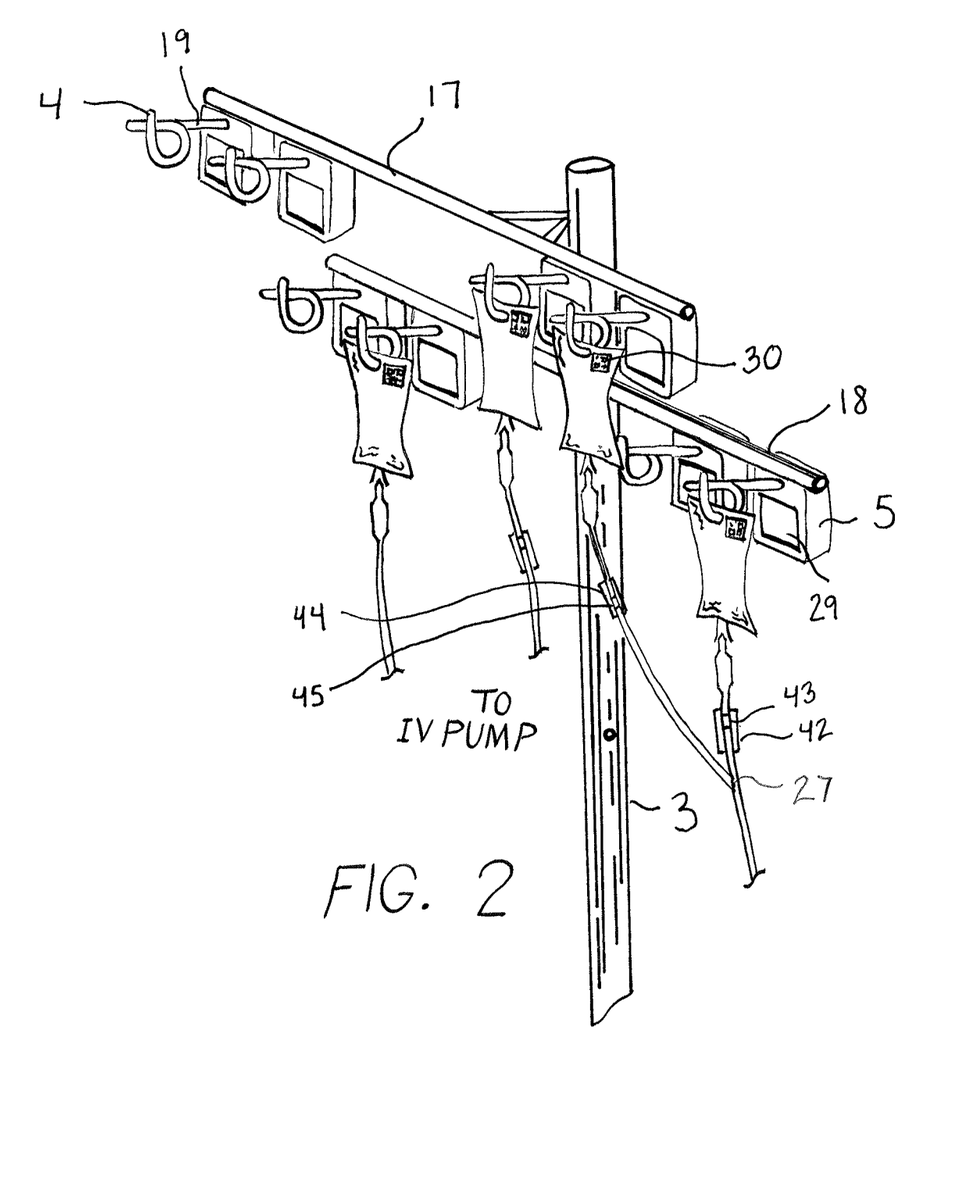
FIG. 2 is a perspective view of portions of the IV pump scanner illustrated in FIG. 1.
Figures 5A, 5B, 5C:
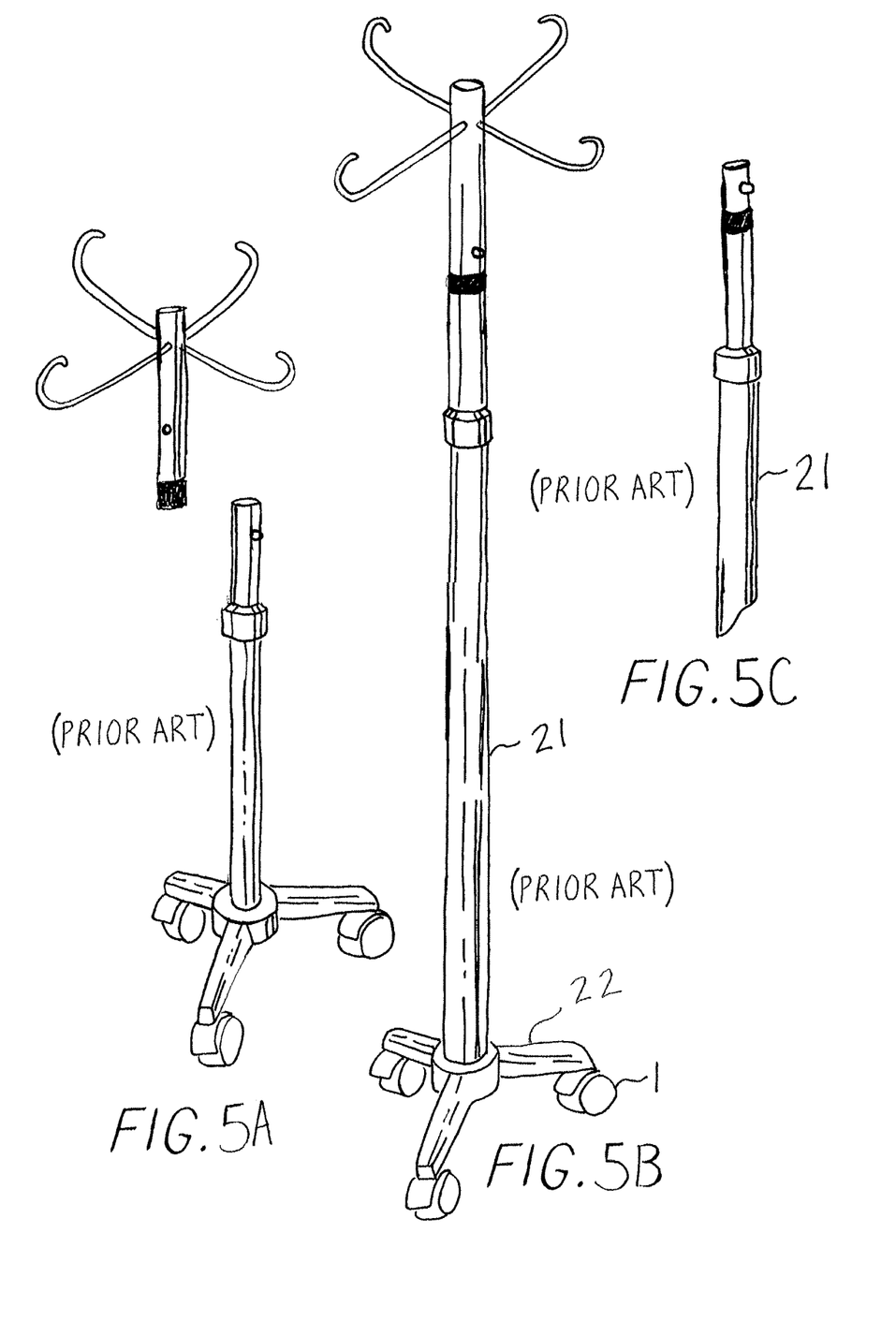
FIGS. 5A, 5B and 5C are perspective views of a prior art IV pole.

In FIG. 1, a metal IV hook 4 is shown. This is where a medication bag hole is placed in order to hang IV fluid 24 or medication 25. In FIG. 1 and FIG. 2, as an example, the modified IV pole supporting frame 3 that holds the supporting poles 17, 18, to hold eight medication scanner housings 5 above pump system 2 is displayed. FIGS. 5A, 5B and 5C represent an IV Pole representing another configuration.

In FIG. 2, FIG. 3A, 3B, and FIG. 4, medication scanner 29, in housing 5, connects with horizontal poles 19. Scanner 29 is connected to internal switch 11 which is actuated when an IV Bag is hung from pole scanner hook 4. Internal switch 11 is coupled to hollow metal tube 19. This internal switch 11 (or multiple internal switches) may be included as a component of a measuring device that monitors forces of compression, tension, shear and/or magnetic force placed by medication IV fluid or medication on hook 4. Switch 11 communicates to a computer system in the IV Pump hardware and software/IV pump system 2 in pump PC 6 by sending data (obtained by converting mechanical force into electrical output signal via data transfer cables 16) inside IV poles 17, 18, 3 as an example of communication.

Figure 4:
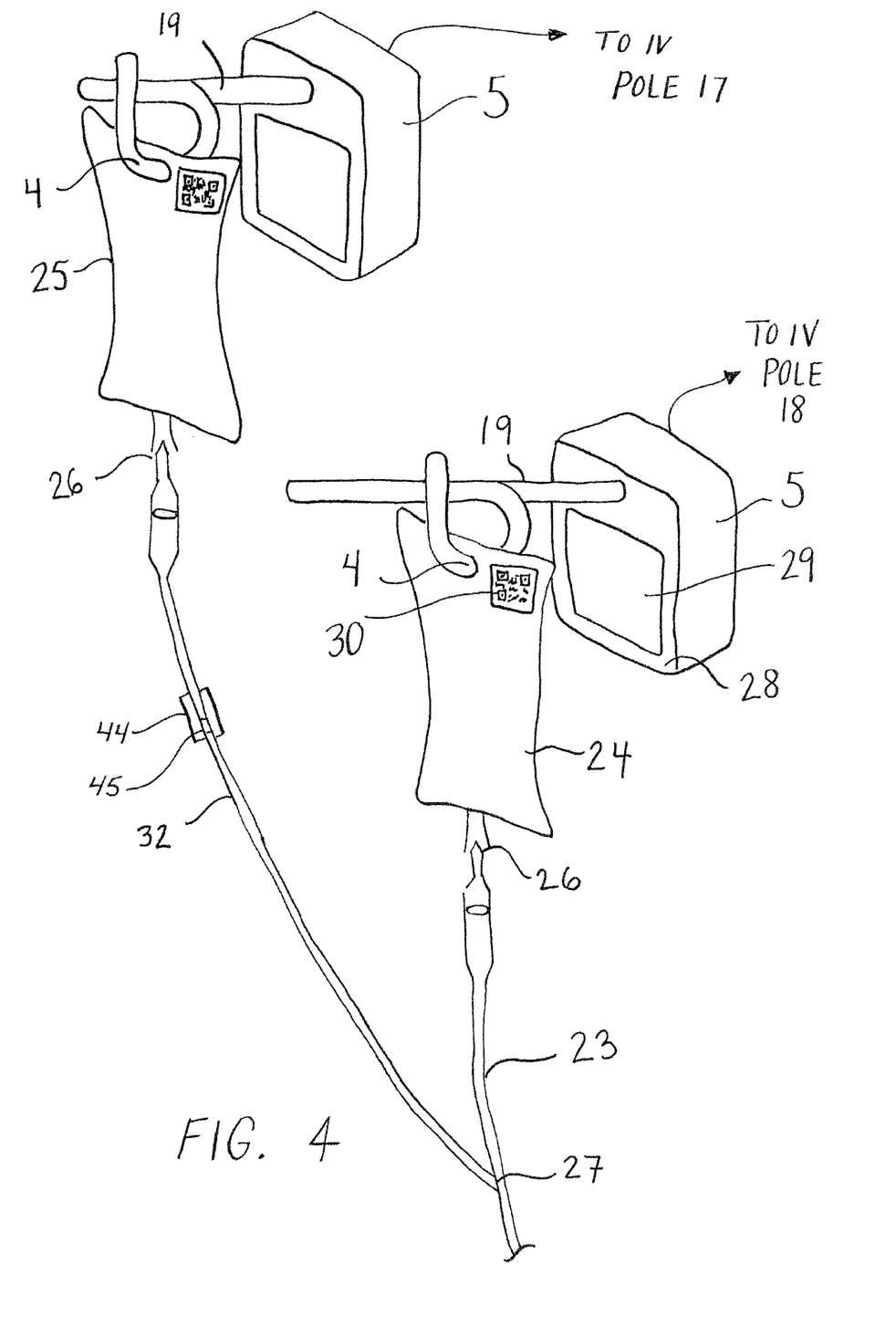
FIG. 4 illustrates structure associated with IV bags in accordance with an exemplary embodiment of the present invention, in a perspective view of an exemplary "column".

In FIG. 3A, 3B, sensing switch 11 is activated by medication pole 19 connected to IV pole hook 4. When medication flow out of the bag moves pole 19 slightly, the switch 11 is used as a type of communication for the pump system 2 pictured in FIGS. 1 and 6. In this manner, pump 2 is alerted when new medication is hung, and may activate the 2D Camera 29 to take picture of 2D bar code 30 as seen in FIG. 2 and FIG. 4 by digital data transfer to initiate data acquisition using the camera. In other words, once switch 11 is actuated, camera 29 scans bar code 30.

An attachment member may be comprised of pole 19 and hook 4. Pole 19 rotates about pivot point 99 that is included in hinge 14. While pivot point 99 is shown approximately centered on pole 19, this is merely exemplary, as pivot point 99 may be located at other locations, including an end of pole 19. Spring 46 maintains pole 19 in the horizontal orientation shown in FIG. 3A. When an IV bag is placed onto hook 4, the weight of the IV bag causes pole 19 to pivot as shown in FIG. 3B. This pivoting is detected as a result of proximity sensors 12 and 13 moving towards each other. Proximity sensors 12 and 13 convert the physical distance between them into electrical signals. As the weight of the IV Bag decreases as medicine is dispensed, proximity sensors 12 and 13 move further apart.

While proximity sensors 12 and 13 are disclosed for measuring movement of the IV bag hanging on hook 4, other methods of measurement may also be used. For example, movement of pole 19 can be measured with an angular sensor.

Optional weight 41 (created by solid metal on distal end of pole 19) places horizontal pole 19 parallel to floor and at an equilibrium when no medication is on the pole hook as seen in FIG. 3A. A proximal end of the pole is where medication is hung 4. The medication container may further include a vertical track forming a press fit with horizontal weighted IV pole 19, the spring 46 and the internal switch 11, as well as proximity sensors 12 and 13.

Figure 6:
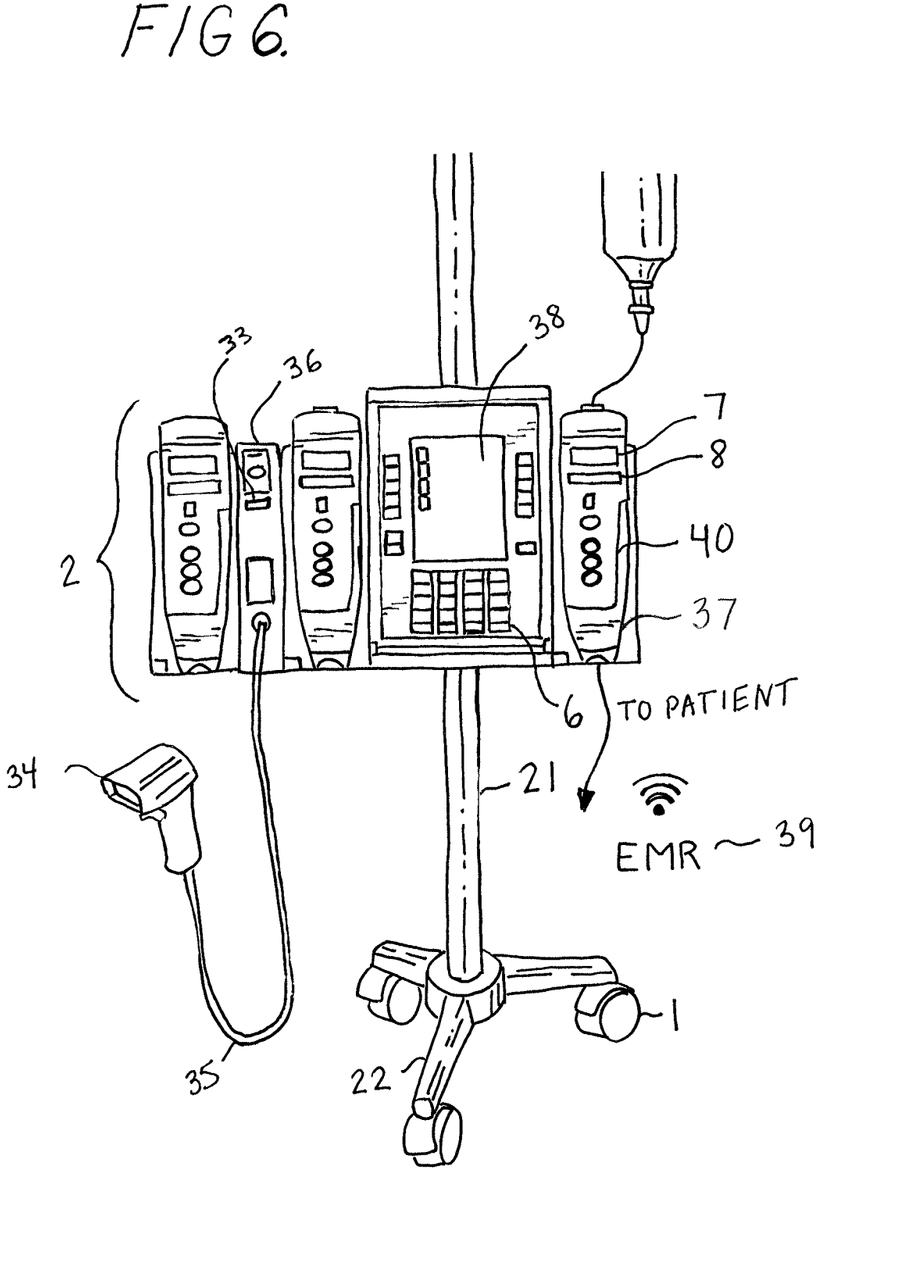
FIG. 6 is an IV pump in accordance with a further exemplary embodiment of the present invention.

In FIG. 3A, 3B, change in spring tension 46 and distance of proximity sensors 12 and 13 notifies IV pump PC 6 that in channel 31 below 2D camera 29 (as an example of channel) IV tubing 23 is actively infusing a medication. Weight sensing switch 11 can detect when a new bag of fluid is hung on pole hook 4 as seen in FIG. 3B, and the pump may be reprogrammed when weight sensing switch detects the bag is removed and replaced—by movement of pole 19 connected to hook (as evidenced by FIG. 3A and FIG. 3B). A compartment is made of plastic 5, and holds 2D camera 29, and lcd display screens 9 on which is displayed the medication name (on front panel 10) seen in FIG. 1. Back panel 28 of medication scanner housing 5, faces IV medication bag and hook 4. In FIG. 1 and FIG. 6, LCD screen 7 displays the medication rate and lcd screen 8 displays medication name. On IV pump channel 31 directly below 2D camera housing 5 being used, for example there are right medication scanners and housings as an example of the medication scanning device 15. IV bag 25 may either enclose IV fluids or IV medication. While a weight activated switch 11 is disclosed in an exemplary embodiment, other methods may be used to detect whether an IV bag is present, including a proximity sensor, toggle switch, pressure sensor by the internal spring, 46 etc. As another alternative to proximity sensors, proximity detection can include a light sensor (that is blocked when the bag is hung in position), sonar, RFID (with an RFID tag included with the bag), etc.

Switch 11 (or alternative embodiments as described above) may also be used to determine if there is patency. Thus, as explained above, if the IV tubing leading from the IV bag to the pump is blocked, and no fluid is flowing to the pump, switch 11 will not detect any change over time, thus indicating that the fluid path from the IV bag is blocked. An alarm may then be generated to indicate that a lack of patency has been detected.

In FIG. 6, a user scans an ID badge on scanner 33 or enters a number code on the pump key pad control panel 6 (or uses some other form of security such as biometrics) to unlock the machine if an ID badge not present it in accordance with steps known in the prior art.

In FIG. 1 and FIG. 6, in order to program IV pump mechanism in IV channel to infuse IV liquid medication 24 and 25, a user scans an ID badge using scanner 33, or uses some other form of security, including biometrics and/or password protection) to use IV pump system 2 to infuse medications (24, 25).

In FIG. 1, IV pump 6 and channels 31 are shown, as seen in frontal view with scanner housing 5 and scanner interface lcd screen 9, scanner hook 4. IV pole design in linear fashion of 17 and 18 is an example of how the medication scanners may be placed. The design is not limited to the drawings displayed. IV pole example in FIGS. 5A, 5B and 5C displays how the top of the IV pole can be replaced, allowing for a modified IV pole and IV pole hook design to comprise of medication scanner in a variety of examples not limited to one depicted in this embodiment.

Medication scanner 2D camera 29 in FIG. 2, FIG. 3A, 3B and FIG. 4 takes a picture of medication bar code 30. IV pump scanner device 15 has scanner compartment 5 holding scanner screen 9 with 2D camera screen 29 as well as connected to horizontal IV pole 19, shown in FIG. 2, to program pump system 2 by 2D barcode 30 directly above IV channel 31. Connection to program IV Pump 2, connected via data transfer cables 16 from 2D camera 29.

Bar code scanning to program the pump is also present in FIG. 6, with scanner 33 or 34 to scan medication bar code. This information may optionally be used to program the rate of IV pump channel 31.

Peripheral IV scanner 34 is designed to scan patient wristband for 2D bar code of patient's ID band or other identifier. IV scanner 34 for patient bar codes can be used in an interchangeable sequence of scanning before medication scanning device 15 scans 2D barcode 30 of medication or fluid scanning before or after. Scanner 34 may be wireless without connecting wire cord 35 as depicted in prior art FIG. 6.

In case of emergency and if patient wrist band for scanning is not yet available or damaged, i.e. a new patient in ER, or water damage to ink on patients bar code, a user may override scanning the wrist band. Peripheral scanner 34 connects with machine scanner channel 36. When another person performs safety checks, they are walked through required protocol on IV pump interface 38 (protocol such as 5 rights protocol is described in prior art). In case of emergency or when patient wristband cannot be scanned, 2D camera 29 for medication can still scan medication bar code or 2D bar code 30 to detect errors via software upgrade with guardrails and pharmacy guidelines. Medication scanner 15 can connection to EMR 39 to detect errors in medication concentration, rate, and drug-drug reactions, regardless of patient identifier as seen in FIG. 1 and FIG. 6.

Scanners 29 integration with optional safety feature is seen in FIG. 3A, 3B. Optional pharmacy infusion recommendations into IV pump system 2 are also contemplated. The front panel 10 of medication scanner, has an lcd display 9 for displaying medication name, to notify IV pump user medication has been scanned and processed. LCD screen 7 may display the letter of the channel 31 that the scanner communicates with. LCD screens on channels 31 below will display rate 7 and medication name 8 on display panels below, when pump has been programmed with the IV medication(s). As an example, linear pole for 2D scanners in housing 5 is to connect to larger horizontal IV pole 18,17. 2D camera is merely an example. Medication scanning device LCD 9 screen displays letter A, B, C or D, to match the correlating channels communicating with channel 31 displaying A, B, C and D prior to programming and scanning as mentioned in prior art.

Channels may be labeled from left to right. In FIG. 1 and FIG. 6, channel 31 would be labeled as D on screen 7 prior to programing the pump as seen in since it is the fourth channel on the right.

In FIG. 6, safety guardrails integrated into pump software inside pump PC 2, displaying on interface 38, will alert medical professions to drug-drug, or drug-IV fluid interactions (via software upgrades, for example) as well as preventing wrong rate for medications as an example of safety alerts and upgrades. IV pump software would notify user by displaying error message on LCD screen 38. The software in the machine of IV pump system 2, integrated with electronic health record EMR 39 may notify a user of unsafe orders, unsafe concentration, unsafe route via IV medication or fluid ordered by resident, NP, PA or attending based on system with medication method explained as seen in prior art of FIG. 6. The software will notify the healthcare provider of safety measures and will not allow for an unsafe IV infusion to infuse.

As seen in FIG. 1 and FIG. 6, a user connects IV tubing 23 into IV channel 31.

As seen in FIG. 1 and FIG. 6, Attachable channel 36 exists for medication scanning and scanner for ID badge 33, and scanner for patient 34, as well as scanner for medication.

In FIG. 1 and FIG. 6, Lever 37 is to open IV channel 31.

When IV fluids or medications are programmed to the pump the user desirably scans badge 33.

Figure 7:
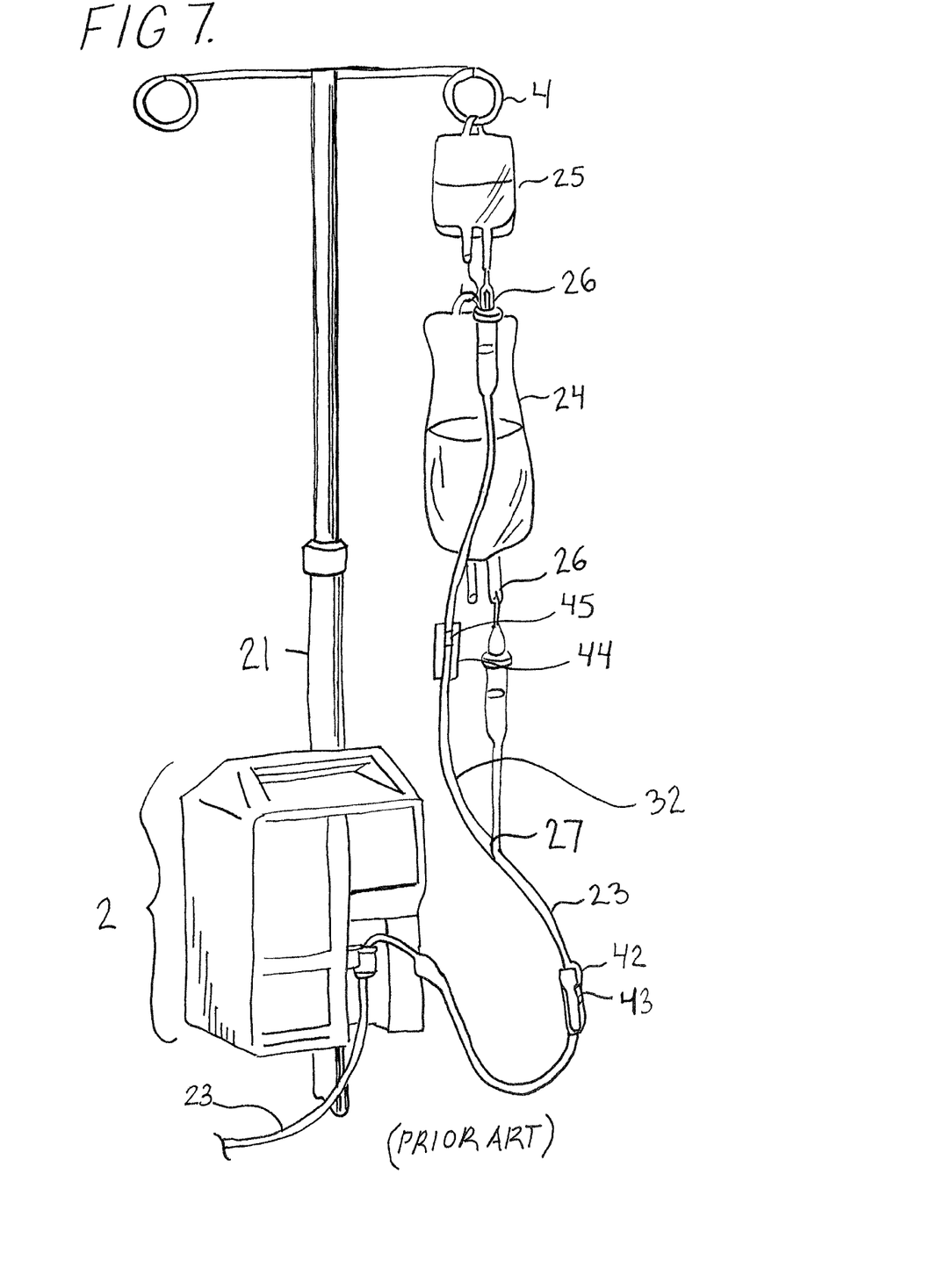
FIG. 7 is a perspective drawing of multiple prior art IV bags.

In FIG. 4 and FIG. 7, IV tubing 23 connection is for piggyback IV solutions at IV port 27. Current IV pumps are unable to detect if a bag above IV pump is clamped when two medication bags (24,25) are connected via IV tubing port 27 infusing into one channel 31. Lack of this safety feature allows for error of non-dilated medication to infused which can result in harm and a medication error, or infusion of fluid without medication as another example.

The power supply for the IV pump is known to one of ordinary skill in the art.

As seen in FIG. 1 and FIGS. 5A, 5B and 5C, IV pole 21 is connected to part of IV pole 3 except without cable communications inside. Separate poles allow for an interchangeable and modifiable design of part 3 connecting with 17 and 18.

In FIG. 6, IV pole base 22 with metal is to prevent tipping of machine when rolled over uneven surface, and to counter weight from top of pole 3 and IV pump system 2. IV pole base 22, connects to wheels 1 as seen in FIG. 1, FIG. 5 and FIG. 6.

FIG. 1 and FIG. 6 include a variable number of wheels and design for IV pole.

3 IV pole connects Scanner safety feature system 15 information with IV pump computer PC 6 via data transfer cables or wirelessly through a network as an example. In FIG. 3A, 3B, the connection comprises (but is not limited to) data transfer cables (USB, Cat6, Cat7, Cat8, Ethernet) 16 from medication scanning device 15 comprising of switch 11 and proximity sensors 12, 13, connecting 2d Camera scanner 29. Medication scanner in FIG. 3A, 3B, may connect to power source 20 via data transfer cables 16 inside poles 17, 18 and section 3, with several examples of charging such as internal battery capable of charging via wall outlet. Power source 20 may be provided by IV pump PC internal battery or wall outlet. In FIG. 1, portion of IV pole 3 with 17 and 18 as an example connected to scanning device system with safety features 15 described herein able to be removed and replaced for maintenance, charge and repair, with another set of scanners.

The hook 4 on pole 19 is where medication (24, 25) is hung. Weight activated switch 11 detects medication hung on pole by moving pole 19. Internal switches 11 activates the channel below 31 to prompt the user to use the channel below to program pump channel directly below 2D camera 29. Software communications with channel labeling such as channel A, B, C, ect, existing in prior art to IV channel lcd screen 7, to match scanner lcd screen 9 to designated channel 31.

In FIG. 1 and FIG. 6, IV pump user desirably opens the door to IV channel 40, by releasing 37 lever, to open channel door to insert IV tubing 23.

In FIG. 7, plastic holder for clamp, 44, of shorter secondary IV tubing 32 exists in current IV tubing design compatible with alaris IV pump to prime tubing, which is involved, in infusing medication or fluid seen in prior art. Primary tubing 23 depicts clamp above another IV pump 42 as well.

Housing for clamp 44 used for priming IV fluid and clamping tube 32 with insert 45 that rolls on track inside 44 for secondary infusion of medication 25. Clamp 42, with internal movable clamp cylinder 43, is for longer primary tubing 23 seen in FIG. 4 and FIG. 7. The medication container is accessed and changed by IV tubing spike 26 uses for IV tubing either 23 or 32 to access fluid to administer. Connection of secondary tubing 32 into primary tubing 23, occurs at port 27 as seen in prior art in FIG. 2, FIG. 4 and FIG. 7.

The IV pump system 2 is used to administer IV medications (24,25) and fluids (24, 25) through controlled pump channel 31 to infuse at a safe rate into a patient's vein via primary IV tubing 23. The medication rate is determined by a doctor's order and pharmacy safety guidelines integrated into EMR 39 seen in prior art FIG. 6. Medication software updated with guardrails and safety features as mentioned in prior art communicates with medication scanner 15. To prevent errors, medication scanner 2D camera 29 have been integrated into the design seen in FIG. 1.

The back panel 28 of medication scanner housing 5 faces where IV medication of fluid is hung. The scanner 34 is designed to scan the patient's ID band (or other forms of identification such as biometrics), but in prior art in FIG. 6 may also be used in some models to scan medication bar code 30. The scanner 34 is connected to the IV Pump PC hardware 6 in the same manner the Alaris model is seen in prior art on FIG. 1 and FIG. 6. The software and hardware inside the computer of the pump with hard drive and lcd screen 38 is evident to one of ordinary skill in the art having read this description and seen FIG. 1 and FIG. 6. A 2D camera 29 is designed to increase compliance to scanning, which is connected to hardware and software of IV pump computer PC via for example pole 3 with a data cable or wireless connection. IV channel 31 below the scanner 29, once 2D barcode 30 on medication bag or Iv fluid is scanned, 2D camera 29, which captures 2D bar code 30, is the future of enhancing compliance to scanning and safety features further reducing human error and patient harm.

While the present invention has been described herein with reference to exemplary embodiments, it should be understood that the invention is not limited thereto. Those skilled in the art with an access to the teachings herein will recognize additional modifications, applications, and embodiments within the scope thereof and additional fields in which the invention would be useful.

The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein, it is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A device for monitoring a liquid medication or fluid being provided to a patient from a first medication storage container via a pump, the first medication storage container including a first scannable code representing identification information regarding a first liquid medication or fluid in the first medication storage container, said device comprising:
   an IV pole assembly including a first hook configured to releasably mount the first medication storage container thereon and being movable from a first rest position before the first medication storage container is mounted thereon to any one of a plurality of second positions in response to the mounting of the first medication storage container thereon and to a change in the amount of the first liquid medication or fluid in the first medication storage container, with the particular one of the plurality of second positions being a function of the amount of the first liquid medication or fluid in the first medication storage container;
   a first scanner mounted on said IV pole assembly and configured for automatically scanning the first scannable code on the first medication container mounted on said first hook when said first hook is in any one of said second positions to provide a first electrical signal representing identification information regarding the first liquid medication or fluid in the first medication storage container;
   a first hook movement detector mounted on said IV pole assembly and configured for automatically detecting the movement of said first hook from said first rest position to any one of said plurality of second positions when said first medication storage container is mounted on said first hook and providing a second electrical signal indicative of the position of said first hook; and
   a receiver for receiving said first and second electrical signals to provide users of said device with information regarding the first liquid medication or fluid being provided to the patient.

2. The device of claim 1, wherein said device comprises a second hook, a second scanner and a second hook movement detector, said second hook being mounted on said IV pole assembly and configured to releasably mount a second medication storage container thereon at a height above the position of the first medication storage container and generally vertically aligned in a column therewith, the second medication storage container including a second scannable code representing identification information regarding a second liquid medication or fluid in the second medication storage container and a second outlet tube through which the second liquid medication or fluid in the second storage container may flow, the first medication storage container having a first outlet tube through which the first liquid medication or fluid in the first storage container may flow, the second outlet tube being connected to the first outlet tube, a clamp interposed between the second outlet tube and the first outlet tube and configured when closed to isolate the second liquid medication or fluid in the second outlet tube from the first liquid medication or fluid in the first outlet tube, and when opened to enable the second liquid medication or fluid in the second outlet tube to mix with the first liquid medication or fluid in the first outlet tube, said second hook being movable from a third rest position before the second medication storage container is mounted thereon to any one of a plurality of fourth positions in response to the mounting of the second medication storage container thereon and to a change in the amount of the second liquid medication or fluid in the second medication storage container, with the particular one of said plurality of fourth positions of said second hook being a function of the amount of the second liquid medication or fluid in the second medication storage container, said second scanner being mounted on said IV pole assembly and configured for automatically scanning the scannable code on the second medication container mounted on said second hook when said second hook is in said any one of said fourth positions to provide a third electrical signal representing identification information regarding the second liquid medication or fluid in the second medication storage container, said second hook movement detector being mounted on said IV pole assembly and configured for automatically detecting the movement of said second hook from said third rest position to any one of said plurality of fourth positions when the second medication storage container is mounted on said second hook and providing a fourth electrical signal indicative of the position of said second hook.

3. The device of claim 2, wherein said receiver is configured for receiving said second electrical signal from said first hook movement detector, for receiving said fourth electrical signal from said second hook movement detector and for generating an error signal if said fourth electrical signal indicates that the second medication storage container is mounted on said second hook but the second liquid medication or fluid is not flowing out of the second medication container for mixing with the first liquid medication or fluid from the first medication storage container.

4. The device of claim 2, wherein said fourth electrical signal enables said receiver to determine the flow rate of the second liquid medication or fluid leaving the second medication storage container over time.

5. The device of claim 2, wherein said receiver is configured for receiving pharmacy data, for comparing the pharmacy data with said third electrical signal, and for generating an error signal if a mismatch is detected from said comparing.

6. The device of claim 1, wherein said first hook movement detector is selected from the group consisting essentially of a proximity sensor, a switch, and an angular sensor.

7. The device of claim 1, wherein said first scanner is configured to scan the first scannable code optically.

8. The device of claim 1, wherein said second electrical signal enables said receiver to determine whether the first liquid medication or fluid is leaving the first medication storage container over time.

9. The device of claim 1, wherein said receiver is configured for receiving pharmacy data, for comparing the pharmacy data with said first electrical signal, and for generating an error signal if a mismatch is detected from said comparing.

10. A method of monitoring a first liquid medication or fluid being provided to a patient from a first medication storage container via a pump, the first medication storage container including a first outlet tube and a first scannable code representing identification information regarding a first liquid medication or fluid in the first medication storage container, the first outlet tube enabling said first liquid medication or fluid to flow therethrough, said method comprising:

mounting said first medication storage container on a first hook of an IV pole assembly, said first hook being movable from a first rest position before said first medication storage container is mounted thereon to any one of a plurality of second positions in response to the mounting of said first medication storage container thereon and to a change in the amount of said first liquid medication or fluid in said first medication storage container, with the particular one of the plurality of second positions being a function of the amount of said first liquid medication or fluid in said first medication storage container;

automatically scanning said first scannable code on said first medication container when said first medication container is mounted on said first hook to provide a first electrical signal representing identification information regarding said first liquid medication or fluid in said first medication storage container;

automatically detecting the movement of said first hook from said first rest position to any one of said plurality of second positions when said first medication storage container is mounted on said first hook and providing a second electrical signal indicative of the position of said first hook; and receiving said first and second electrical signals to provide users with information about said first liquid medication or fluid being provided to said patient.

11. The method of claim 10 additionally comprising:
providing a second medication storage container including a second liquid medication or fluid and a second scannable code representing identification information regarding said second liquid medication or fluid in said second medication storage container;

releasably mounting said second medication storage container on a second hook of said IV pole assembly at a height above a position of said first medication storage container on said IV pole assembly and generally vertically aligned therewith, said second medication storage container including a second outlet tube through which said second liquid medication or fluid in said second storage container may flow, said second hook being movable from a third rest position before said second medication storage container is mounted thereon to any one of a plurality of fourth positions in response to the mounting of said second medication storage container thereon and to a change in the amount of said second liquid medication or fluid in said second medication storage container, with the particular one of said plurality of fourth positions of said second hook being a function of the amount of said second liquid medication or fluid in said second medication storage container;

connecting said second outlet tube to said first outlet tube of said first medication storage container, with a clamp interposed between said second outlet tube and said first outlet tube, said first outlet tube enabling said first liquid medication or fluid in the first storage container to flow therein;

closing said clamp to isolate said second liquid medication or fluid in said second outlet tube from said first liquid medication or fluid in said first outlet tube;

opening said clamp to enable said second liquid medication or fluid in said second outlet tube to mix with said first liquid medication or fluid in said first outlet tube;

automatically scanning said second scannable code on said second medication container when said second medication container is mounted on said second hook to provide a third electrical signal representing identification information regarding said second liquid medication or fluid in said second medication storage container;

automatically detecting the movement of said second hook from said third rest position to any one of said plurality of fourth positions when said second medication storage container is mounted on said second hook and providing a fourth electrical signal indicative of the position of said second hook; and receiving said third and fourth electrical signals to provide users with information about said second medication or fluid being provided to said patient.

12. The method of claim 11, additionally comprising:
generating an error signal if said fourth electrical signal indicates that said second medication storage container is mounted on said second hook but said second liquid medication or fluid is not flowing out of said second medication container for mixing with said first liquid medication or fluid from said first medication storage container.

13. The method of claim 11, additionally determining whether said second liquid medication or fluid is leaving said second medication storage container over time.

14. The method of claim 13, additionally comprising:
determining the flow rate of said second liquid medication or fluid leaving said second medication storage container over time.

15. The method of claim 11, additionally comprising:
receiving pharmacy data, comparing said pharmacy data with said third electrical signal, and generating an error signal if a mismatch is detected from said comparing.

16. The method of claim 10, wherein the movement of said first hook from said first rest position to any one of said second positions is accomplished by any one of the group consisting essentially of a proximity sensor, a switch, and an angular sensor.

17. The method of claim 10, wherein said automatic scanning of said first scannable code is accomplished optically.

18. The method of claim 10, additionally determining whether said first liquid medication or fluid is leaving said first medication storage container over time.

19. The method of claim 18, additionally comprising:
determining the flow rate of said first liquid medication or fluid leaving said first medication storage container over time.

20. The method of claim 10, additionally comprising:
receiving pharmacy data, comparing said pharmacy data with said first electrical signal, and generating an error signal if a mismatch is detected from said comparing.

* * * * *